United States Patent [19]

Gorman et al.

[11] Patent Number: 4,542,125

[45] Date of Patent: Sep. 17, 1985

[54] ANTIMICROBIAL SURFACE DEGERMING COMPOSITIONS AND METHOD OF USE THEREOF

[75] Inventors: William G. Gorman, East Greenbush; Karl F. Popp, Schodack; Jennifer C. Galloway, Kinderhook; David M. Sedlock, Bethlehem, all of N.Y.

[73] Assignee: Sterling Drug Inc., New York, N.Y.

[21] Appl. No.: 592,963

[22] Filed: Mar. 23, 1984

[51] Int. Cl.$^4$ ................. A01N 31/00; A61K 31/70
[52] U.S. Cl. ......................... 514/57; 514/332; 546/264
[58] Field of Search ............ 424/263, 326, 180; 546/264

[56] References Cited

U.S. PATENT DOCUMENTS

| | | | |
|---|---|---|---|
| 3,055,902 | 9/1962 | Walker | 260/293 |
| 3,472,840 | 10/1969 | Stone et al. | 260/231 |
| 4,045,483 | 8/1977 | Cutler et al. | 260/552 R |
| 4,206,215 | 6/1980 | Bailey | 424/263 |
| 4,420,484 | 12/1983 | Gorman et al. | 424/326 |

FOREIGN PATENT DOCUMENTS

| | | | |
|---|---|---|---|
| 1528558 | 6/1968 | France | 546/264 |
| 930040 | 7/1963 | United Kingdom | 546/264 |

OTHER PUBLICATIONS

CTFA Cosmetic Ingredient Dictionary, (3rd Ed.), pp. 54, 56, 94, 95, 175 and 245, (1982).

*Primary Examiner*—Delbert R. Phillips
*Assistant Examiner*—Charles H. Thieman
*Attorney, Agent, or Firm*—Theodore C. Miller; Paul E. Dupont; B. Woodrow Wyatt

[57] ABSTRACT

Antimicrobial surface degerming compositions comprising a bis[4-(substituted-amino)-1-pyridinium]alkane, especially octenidine hydrochloride, as the antimicrobial agent, one or more compounds selected from the group consisting of higher-alkyldilower-alkylamine oxides, higher-alkylaminoalkanoic acids, higher-alkyldiloweralkylammoniumalkanoate betaines and quaternary nitrogen-containing cellulose ethers, and an aqueous vehicle, especially antimicrobial skin cleansing compositions and antimicrobial bovine teat dip compositions, and method of use thereof are disclosed.

12 Claims, No Drawings

ANTIMICROBIAL SURFACE DEGERMING COMPOSITIONS AND METHOD OF USE THEREOF

BACKGROUND OF THE INVENTION

1. Field of the Invention

The invention relates to antimicrobial surface degerming compositions containing as the antimicrobial agent a bis[4-(substituted-amino)-1-pyridinium]alkane, especially antimicrobial skin cleansing compositions and antimicrobial bovine teat dip compositions, and method of use thereof.

2. Information Disclosure Statement

Bailey U.S. Pat. No. 4,206,215 issued June 3, 1980 describes antimicrobial bis[4-(substituted-amino)-1-pyridinium]alkanes and states at column 10, lines 24–30, that they can be formulated with any compatible, pharmaceutically acceptable surfactant preferably a non-ionic surfactant such as the polyoxyethylene polyoxypropylene copolymers described in U.S. Pat. No. 3,855,140, amine oxides such as stearyl dimethyl amine oxide described in U.S. Pat. No. 3,296,145 and the like or with mixtures of these but does not specifically describe any such compositions. Example 10 describes 1,10-bis[4-(octylamino)-1-pyridinium]decane dichloride, whose generic name is octenidine hydrochloride.

Gorman et al. U.S. Pat. No. 4,420,484 issued Dec. 13, 1983 describes antimicrobial skin cleansing compositions containing among other antimicrobial agents a bis[4-(substituted-amino)-1-pyridinium]alkane and a polyethylene glycol ester surfactant—betaine and/or amine oxide surfactant combination. Compositions containing octenidine hydrochloride as the antimicrobial agent are specifically described.

The higher-alkyldilower-alkylamine oxides are a known class of surfactants of the nonionic type. The higher-alkylaminoalkanoic acids and higher-alkyldiloweralkylammoniumalkanoate betaines are known classes of surfactants of the amphoteric type. Specific examples of these surfactants are described by generic name (CTFA Adopted Name), trade name and structural formula by CTFA Cosmetic Ingredient Dictionary (Third Edition, 1982; published by The Cosmetic, Toiletry and Fragrance Association, Inc., 1110 Vermont Avenue, N.W., Washington, D.C. 20005) and are commercially available.

Stone et al. U.S. Pat. No. 3,472,840 issued Oct. 14, 1969 describes quaternary nitrogen-containing cellulose ethers, specific examples of which are described by the above-cited CTFA Cosmetic Ingredient Dictionary and are commercially available.

SUMMARY OF THE INVENTION

In a composition of matter aspect the invention is an antimicrobial surface degerming composition comprising (A) from about 0.01% to about 10% by weight of a bis[4-(R-amino)-1-pyridinium]alkane salt having the structural formula

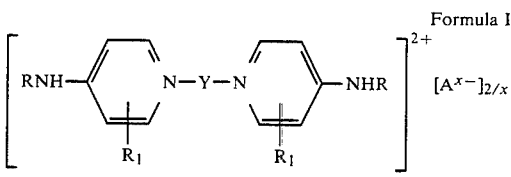

Formula I wherein

Y is alkylene having from 4 to 18 carbon atoms and separating the two 4-(R-amino)-1-pyridinium groups by from 4 to 18 carbon atoms;

R is the same in both occurrences and is alkyl having from 6 to 18 carbon atoms, cycloalkyl having from 5 to 7 carbon atoms, benzyl or phenyl substituted by methylenedioxy or one or two substituents selected from the group consisting of halo, lower-alkyl, lower-alkoxy, nitro, cyano and trifluoromethyl;

$R_1$ is the same in both occurrences and is hydrogen or lower-alkyl; $A^{x-}$ is a pharmaceutically acceptable anion; and x is the valence of the anion;

(B) from about 1% to about 50% by weight of one or more compounds selected from the group consisting of (a) a higher-alkyldilower-alkylamine oxide having the structural formula

Formula II wherein $R_1$ is alkyl having from 8 to 18 carbon atoms or $R_4CONH(CH_2)_3$ wherein $R_4$ is alkyl having from 8 to 18 carbon atoms, R taken alone is methyl, ethyl or 2-hydroxyethyl, $R_3$ taken alone is methyl, ethyl or 2-hydroxyethyl, $R_2$ and $R_3$ taken together with N are morpholino, and wherein 2-hydroxyethyl can be condensed with from 1 to 200 molecules of ethylene oxide;

(b) a higher-alkylaminoalkanoic acid having the structural formula

Formula III wherein R is alkyl or alkenyl having from 8 to 18 carbon atoms, R' is hydrogen or $(CH_2)_n$—COOH and n is an integer from 1 to 5 or an alkali metal salt thereof;

(c) a higher-alkyldilower-alkylammoniumalkanoate betaine having the structural formula

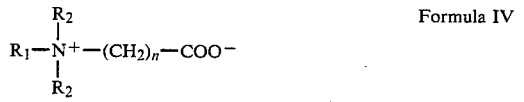

Formula IV wherein $R_1$ is alkyl, alkenyl or alkylbenzyl having from 8 to 18 carbon atoms, $R_2$ is methyl, ethyl, hydroxyethyl or hydroxyethyl condensed with from 1 to 200 molecules of ethylene oxide, propylene oxide or butylene oxide, and n is an integer from 1 to 5;

(d) a quaternary nitrogen-containing cellulose ether having the structural formula

Formula V wherein $R_{cell}$ is the residue of an anhydroglucose unit $(C_6H_{10}O_5)$, x represents the degree of polymerization and is an integer from about 50 to about 20,000 and preferably from about 200 to about 5,000, the R's are the same or different and R has the structural formula

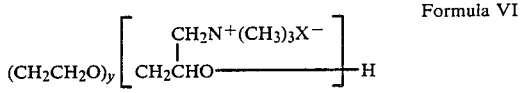

Formula VI wherein y is an integer from 0 to 10, z is an integer from 0 to 3 and $X^-$ is a pharmaceutically acceptable anion; and (C) an aqueous vehicle.

In a process aspect the invention is the method of degerming a living or nonliving surface which comprises applying to the surface an antimicrobially effective amount of a composition according to the composition aspect of the invention.

In a preferred process aspect the invention is the method of preventing or treating mastitis in a cow which comprises applying to the teats of the cow after milking a composition according to the composition aspect of the invention.

In a preferred composition aspect the invention is an above-described composition wherein the compound of part B is a higher-alkylaminoalkanoic acid of Formula III and/or a quaternary nitrogen-containing cellulose ether of Formula V.

DETAILED DESCRIPTION OF THE INVENTION INCLUSIVE OF THE PREFERRED EMBODIMENTS

Definitions of Variables

In Formula I Y is alkylene and is a bivalent saturated aliphatic hydrocarbon group containing from 4 to 18, preferably from 8 to 12, carbon atoms arranged in a branched or unbranched chain and separating the two 4-(R-amino)-1-pyridinium groups by from 4 to 18, preferably from 8 to 12, carbon atoms, for example, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,13-tridecylene, 1,14-tetradecylene, 1,15-pentadecylene, 1,16-hexadecylene, 1,17-heptadecylene, 1,18-octadecylene, 1-methyl-1,4-butylene, 3-methyl-1,5-pentylene, 2-ethyl-1,4-butylene, 3-methyl-1,6-hexylene, 2,4-dimethyl-1,5-pentylene, 1-methyl-1,7-heptylene, 3-ethyl-1,6-hexylene, 3-propyl-1,5-pentylene, 4,4-dimethyl-1,7-heptylene, 2,6-dimethyl-1,7-heptylene, 2,4,4-trimethyl-1,6-hexylene, 2,7-dimethyl-1,8-octylene, 1-methyl-1,10-decylene, 5-ethyl-1,9-nonylene, 3,3,6,6-tetramethyl-1,8-octylene, 3,8-dimethyl-1,10-decylene, 3-methyl-1,11-undecylene, 6-methyl-1,12-dodecylene, 2-methyl-1,13-tridecylene, 4,9-dimethyl-1,12-dodecylene, 4-methyl-1,14-tetradecylene, 2,13-dimethyl-1,14-tetradecylene, 1,4-dipropyl-1,4-butylene, 3-(3-pentyl)-1,5-pentylene, 2-(4,8-dimethylnonyl)-1,4-butylene or 1-heptyl-1,5-pentylene.

In Formula I when R is alkyl containing from 6 to 18 carbon atoms, it can be branched or unbranched, preferably contains from 7 to 9 carbon atoms and is, for example, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, 1-methylpentyl, 2,2-dimethylbutyl, 2-methylhexyl, 1,4-dimethylpentyl, 2-ethylpentyl, 3-ethylpentyl, 2-methylheptyl, 1-ethylhexyl, 2-ethylhexyl, 2-propylpentyl, 2-methyl-3-ethylpentyl, 3-ethylheptyl, 1,3,5-trimethylhexyl, 1,5-dimethyl-4-ethylhexyl, 2-propylheptyl, 5-methyl-2-butylhexyl, 2-propylnonyl, 2-butyloctyl, 1,1-dimethylundecyl, 2-pentylnonyl, 1,2-dimethyltetradecyl or 1,1-dimthylpentadecyl.

In Formula I when R is cycloalkyl containing from 5 to 7 carbon atoms, it is, for example, cyclopentyl, cyclohexyl or cycloheptyl.

In Formula I when R is phenyl substituted by methylenedioxy or one or two substituents selected from the group consisting of halo, lower-alkyl, lower-alkoxy, nitro, cyano and trifluoromethyl, it is, for example, p-chlorophenyl, o-chlorophenyl, m-chlorophenyl, p-bromophenyl, m-fluorophenyl, p-iodophenyl, 2,4-dichlorophenyl, 2,4-difluorophenyl, 2,5-dibromophenyl, 3,5-dichlorophenyl, 3-chloro-4-fluorophenyl, 3,4-methylenedioxyphenyl, p-ethylphenyl, p-methoxyphenyl, m-nitrophenyl, o-cyanophenyl, m-(trifluoromethyl)phenyl or 2-methoxy-5-methylphenyl.

In Formula I when R is benzyl and phenyl group can also be substituted by one or two substituents, for example, halo, hydroxy, lower-alkyl, lower-alkoxy, nitro, cyano or trifluoromethyl.

In Formula I halo is fluoro, chloro, bromo or iodo. Lower-alkyl and lower-alkoxy have from one to four carbon atoms. Lower-alkyl is thus methyl, ethyl, propyl, isopropyl, butyl, isobutyl, sec-butyl or tert-butyl. Lower-alkoxy is thus methoxy, ethoxy, propoxy, isopropoxy, butoxy, isobutoxy, sec-butoxy or tert-butoxy.

A preferred compound of Formula I is that wherein Y is 1,10-decylene, R is octyl, $R_1$ is hydrogen, $A^{x-}$ is chloride ion and x is 1, which is the compound of parts A and B of Example 10 of above-cited U.S. Pat. No. 4,206,215 described as 1,10-bis[4-(octylamino)-1-pyridinium]decane dihydrochloride and whose generic name is octenidine hydrochloride.

$R_1$ or $R_4$ of Formula II, R of Formula III or $R_1$ of Formula IV can be branched or unbranched alkyl or alkenyl of 8 to 18 carbon atoms. Unbranched alkyl having an even number of carbon atoms is preferred, especially dodecyl (lauryl), tetradecyl (myristyl), hexadecyl (cetyl) and octadecyl (stearyl).

The preferred compounds of Formula II–VI are identified below by CTFA Adopted Names as listed in the above-cited CTFA Cosmetic Ingredient Dictionary. A preferred higher-alkyldiloweralkylamine oxide of Formula II is Myristamine Oxide wherein $R_1$ is myristyl and $R_2$ and $R_3$ are each methyl. A preferred higher-alkylaminoalkanoic acid of Formula III is Cocaminopropionic Acid wherein R is the coconut radical (about 48% lauryl, 18% myristyl, 8% octyl, 8% cetyl, 7% decyl, 6% oleyl, 3% linoleyl and 2% stearyl), R' is hydrogen and n is 2. A preferred higher-alkyldiloweralkylammoniumalkanoate betaine of Formula IV is a Coco-Betaine wherein $R_1$ is the coconut radical, $R_2$ is methyl and n is 1. A preferred quaternary nitrogen-containing cellulose ether of Formula V is Polyquaternium-10 (Union Carbide UCARE Polymer JR-30M and UCARE Polymer JR-125).

The aqueous vehicle of the composition aspect of the invention is preferably water alone but can also include a pharmaceutically acceptable, water miscible organic diluent, for example, ethyl alcohol, isopropyl alcohol, propylene glycol or glycerin, or a mixture thereof.

The Compositions and Processes

In addition to the above-described ingredients the compositions may also include pharmaceutical adjuncts, for example, humectants, emollients, lubricants, stabilizers, dyes, perfumes and preservatives. In spite of the presence of the antimicrobial agent a preservative may be necessary to prevent growth of microorganisms in the compositions. A pharmaceutically acceptable acid or base for pH adjustment and/or a pharmaceutically acceptable buffer for pH maintenance may also be added.

The process aspects of the invention are carried out by known methods. Living surfaces include those of plants and animals, especially mammal skin, most especially teats of cows. Nonliving surfaces include hard and soft surfaces, for example, those of wood, metal, glass, ceramic, plastic, paper and cloth objects. The compositions are applied to the surfaces by conventional techniques including dipping, swabbing, spraying and scrubbing.

As stated above the invention relates to anti-microbial surface degerming compositions, especially anti-microbial skin cleansing compositions and antimicrobial bovine teat dip compositions. In the following examples Examples 1–5 illustrate basic antimicrobial surface degerming compositions, Examples 6–12 illustrate antimicrobial skin cleansing compositions, and Examples 13–18 illustrate antimicrobial bovine teat dip compositions.

EXAMPLE 1

| Ingredient | Percent by Weight |
| --- | --- |
| Octenidine Hydrochloride | 0.200 |
| Coco-Betaine | 1.80 |
| Purified Water to make | 100.0 |

EXAMPLE 2

| Ingredient | Percent by Weight |
| --- | --- |
| Octenidine Hydrochloride | 0.200 |
| Myristamine Oxide | 1.80 |
| Purified Water to make | 100.0 |

EXAMPLE 3

| Ingredient | Percent by Weight |
| --- | --- |
| Octenidine Hydrochloride | 0.200 |
| Polyquaternium-10 (UCARE Polymer JR 30 M) | 0.550 |
| Purified Water to make | 100.0 |

EXAMPLE 4

| Ingredient | Percent by Weight |
| --- | --- |
| Octenidine Hydrochloride | 0.200 |
| Cocaminopropionic Acid | 1.8 |
| Sodium Hydroxide to make pH 7.0 | — |
| Purified Water to make | 100.0 |

EXAMPLE 5

| Ingredient | Percent by Weight |
| --- | --- |
| Octenidine Hydrochloride | 0.200 |
| Cocaminopropionic Acid | 1.8 |
| Polyquaternium-10 (UCARE Polymer JR 30 M) | 0.550 |
| Sodium Phosphate | 0.280 |
| Sodium Hydroxide to make pH 7.0 | — |
| Purified Water to make | 100.0 |

EXAMPLE 6

| Ingredient | Percent by Weight |
| --- | --- |
| Octenidine Hydrochloride | 2.00 |
| Cocaminopropionic Acid | 5.00 |
| Sodium Phosphate | 0.276 |
| Sodium Hydroxide to make pH 7.0 | — |
| Purified Water to make | 100.0 |

EXAMPLE 7

| Ingredient | Percent by Weight |
| --- | --- |
| Octenidine Hydrochloride | 2.00 |
| Coco-Betaine | 5.00 |
| Sodium Phosphate | 0.276 |
| Sodium Hydroxide to make pH 7.0 | — |
| Purified Water to make | 100.0 |

EXAMPLE 8

| Ingredient | Percent by Weight |
| --- | --- |
| Octenidine Hydrochloride | 2.00 |
| Myristamine Oxide | 5.00 |
| Sodium Phosphate | 0.276 |
| Sodium Hydroxide to make 7.0 | — |
| Purified Water to make | 100.0 |

EXAMPLE 9

| Ingredient | Percent by Weight |
| --- | --- |
| Octenidine Hydrochloride | 2.00 |
| Cocaminopropionic Acid | 4.00 |
| Polyquaternium-10 (UCARE Polymer JR 125) | 2.00 |
| Sodium Hydroxide to make pH 6.5 | — |
| Purified Water to make | 100.0 |

EXAMPLE 10

| Ingredient | Percent by Weight |
| --- | --- |
| Octenidine Hydrochloride | 2.00 |
| Cocaminopropionic Acid | 4.00 |
| Polyquaternium-10 (UCARE Polymer JR 125) | 0.750 |
| Sodium Phosphate | 0.276 |
| Sodium Hydroxide to make pH 6.5 | — |
| Purified Water to make | 100.0 |

EXAMPLE 11

| Ingredient | Percent by Weight |
| --- | --- |
| Octenidine Hydrochloride | 2.00 |
| Coco-Betaine | 7.00 |
| Polyquaternium-10 (UCARE Polymer JR 125) | 2.00 |
| Sodium Phosphate | 0.276 |
| Sodium Hydroxide to make pH 6.5 | — |

-continued

| Ingredient | Percent by Weight |
| --- | --- |
| Purified Water to make | 100.0 |

EXAMPLE 12

| Ingredient | Percent by Weight |
| --- | --- |
| Octenidine Hydrochloride | 2.00 |
| Coco-Betaine | 7.00 |
| Polyquaternium-10 | 0.700 |
| (UCARE Polymer JR 30 M) | |
| Sodium Phosphate | 0.276 |
| Sodium Hydroxide to make pH 6.5 | — |
| Purified Water to make | 100.0 |

EXAMPLE 13

| Ingredient | Percent by Weight |
| --- | --- |
| Octenidine Hydrochloride | 0.200 |
| Cocaminopropionic Acid | 4.50 |
| Propylene Glycol | 4.00 |
| Phenoxyethanol | 0.500 |
| Sodium Phosphate | 0.276 |
| Dye | 0.0125 |
| Sodium Hydroxide to make pH 6.5 | — |
| Purified Water to make | 100.0 |

EXAMPLE 14

| Ingredient | Percent by Weight |
| --- | --- |
| Octenidine Hydrochloride | 0.500 |
| Cocaminopropionic Acid | 4.50 |
| Propylene Glycol | 4.00 |
| Phenoxyethanol | 0.500 |
| Sodium Phosphate | 0.276 |
| Dye | 0.0125 |
| Sodium Hydroxide to make pH 6.5 | — |
| Purified Water to make | 100.0 |

EXAMPLE 15

| Ingredient | Percent by Weight |
| --- | --- |
| Octenidine Hydrochloride | 0.200 |
| Propylene Glycol | 5.00 |
| Coco-Betaine | 2.22 |
| Polyquaternium-10 | 0.550 |
| (UCARE Polymer JR 30 M) | |
| DMDM Hydantoin | 0.500 |
| Sodium Phosphate | 0.276 |
| Dye | 0.00600 |
| Sodium Hydroxide to make pH 6.5 | — |
| Purified Water to make | 100.0 |

EXAMPLE 16

| Ingredient | Percent by Weight |
| --- | --- |
| Octenidine Hydrochloride | 0.500 |
| Propylene Glycol | 5.00 |
| Coco-Betaine | 2.22 |
| Polyquaternium-10 | 0.550 |
| (UCARE Polymer JR 30 M) | |
| DMDM Hydantoin | 0.500 |
| Sodium Phosphate | 0.276 |
| Dye | 0.00600 |
| Sodium Hydroxide to make pH 6.5 | — |

-continued

| Ingredient | Percent by Weight |
| --- | --- |
| Purified Water to make | 100.0 |

EXAMPLE 17

| Ingredient | Percent by Weight |
| --- | --- |
| Octenidine Hydrochloride | 0.200 |
| Propylene Glycol | 4.00 |
| Cocaminopropionic Acid | 1.80 |
| Sodium Chloride | 0.750 |
| Phenoxyethanol | 0.500 |
| Dye | 0.0125 |
| Triethanolamine to make pH 7.0 | — |
| Purified Water to make | 100.0 |

EXAMPLE 18

| Ingredient | Percent by Weight |
| --- | --- |
| Octenidine Hydrochloride | 1.60 |
| Propylene Glycol | 32.0 |
| Cocaminopropionic Acid | 14.4 |
| Sodium Chloride | 6.00 |
| Phenoxyethanol | 4.00 |
| Dye | 0.100 |
| Triethanolamine to make pH 7.5 | — |
| Purified Water to make | 100.0 |

Biological Properties of the Compositions

Excised Porcine Skin Disk Dip Test

Sterile excised porcine skin disks 10 mm. in diameter were inoculated with 20 $\mu$l. of freshly prepared *Staphylococcus aureus* ATCC 27543 culture containing about $10^8$ colony-forming units/ml. and allowed to air dry 15 min. Each disk was then dipped in 2 ml. of one of the compositions of Examples 1–5 and 17 or in 25 mM aqueous potassium dihydrogen phosphate as a control solution, immediately removed, blotted on sterile filter paper, incubated at room temperature for 10 min., swirled for 30 sec. in 10 ml. of a medium of tryptose phosphate broth containing 0.1% lecithin, 0.8% polysorbate 80, 0.25% Tamol-N Micro brand of condensed naphthalenesulfonic acid sodium salt anionic dispersant and 0.1% sodium thiosulfate, and discarded.

To determine the number of surviving bacteria successive tenfold dilutions of neutralized aliquots of the medium in which the disks were swirled were plated on soybean-casein digest agar medium by the pour plate technique. The plates were incubated at 37° C. and counted. Mean $\log_{10}$ counts and reductions of counts from the control were determined and analyzed statistically. The following results were obtained using ten disks for each of the control solution and the tested compositions. Compared with the control solution the compositions of all of Examples 1–5 and 17 produced significant reductions of counts. The results for Examples 1–5 as a group are not significantly different and the results for Examples 4 and 17 as a group are not significantly different.

| Example | Mean Log₁₀ Count of Bacteria Recovered/Disk | Mean Log₁₀ Count Reduction of Bacteria from Control/Disk |
| --- | --- | --- |
| Control | 5.41 ± 0.05 | 0.00 ± 0.05 |
| 1 | 3.58 ± 0.14 | 1.83 ± 0.05 |
| 2 | 3.43 ± 0.07 | 1.98 ± 0.07 |
| 3 | 3.59 ± 0.11 | 1.83 ± 0.11 |
| 4 | 3.72 ± 0.15 | 1.69 ± 0.15 |
| 5 | 3.66 ± 0.14 | 1.76 ± 0.14 |
| 17 | 4.07 ± 0.14 | 1.34 ± 0.14 |

Monkey Paw Scrub Test

The antimicrobial effect of the compositions of Examples 6–12 on the normal bacterial flora of the hands and feet of anesthetized cynomolgous monkeys was measured. Each hand or foot was tested separately and randomly and was first scrubbed for two minutes with Camay brand of bar soap in warm tap water, rinsed for one minute in running warm tap water, washed for two minutes with Camay brand of bar soap in warm tap water, rinsed for two minutes in running warm tap water, and dried with a sterile towel, then sampled for microflora before being scrubbed with the test composition.

Sampling was done by placing a sterile latex surgical glove over the hand or foot, pouring into the glove 100 ml. of aqueous phosphate buffered (0.07M, pH 7.8) sampling fluid containing Triton X-100 brand of polyethylene glycol p-isooctylphenyl ether (0.1%), massaging the hand or foot in the sampling fluid for one minute, and diluting an aliquot (10 ml.) of the sampling fluid with an equal volume of aqueous phosphate buffered (pH 7.2) Tamol-N Micro brand of condensed naphthalenesulfonic acid sodium salt anionic dispersant (2%) neutralizer solution. The volume of the neutralized sample was thus 20 ml.

The hand or foot was then washed for 45 seconds and scrubbed for 15 seconds with 5 ml. of the test composition, rinsed for 30 seconds under warm running tap water, washed for 90 seconds and scrubbed for 30 seconds with an additional 5 ml. of the test composition, rinsed again for 30 seconds under warm running tap water, dried with a sterile towel, and sampled again. This procedure was repeated three times for a total of four times during eight hours with a minimum of one hour between procedures (scrubs). No sample was taken after the third scrub.

Triplicate aliquots (1 ml. each) of each neutralized sample and each of three successive tenfold dilutions thereof were then plated by the pour-plate technique on soybean-casein digest agar. The plates were incubated aerobically at 37° C. for 48–72 hours, then counted using an automated colony counter (Model 880 Artek Systems Corp.) interfaced with a computer (PDP 15), whereby the data were processed by program and expressed as mean log₁₀ counts for each hand or foot and each of the four sampling times and as mean log₁₀ count reductions from after the bar soap scrub and before the first test composition scrub (Pre Scrub 1) to after the first (Post Scrub 1), second (Post Scrub 2) and fourth (Post Scrub 4) test composition scrubs, and overall mean log₁₀ count reductions.

The following results were obtained. The compositions of Examples 6–8 were tested using both hands and feet (n=36, A) and the results for hands were segregated (n=18, B). A corresponding composition not containing any surfactant served as the control for Examples 6–8 (n=36 for both hands and feet, n=17 for hands only). The compositions of Examples 9–12 were tested using only hands (n=20).

| | Mean Log₁₀ Count | | | |
| --- | --- | --- | --- | --- |
| Example | Pre Scrub 1 | Post Scrub 1 | Post Scrub 2 | Post Scrub 4 |
| Control$^A$ | 6.93 | 5.36 | 4.66 | 3.60 |
| 6$^A$ | 7.04 | 5.68 | 5.00 | 3.77 |
| 7$^A$ | 6.97 | 5.63 | 5.08 | 3.70 |
| 8$^A$ | 6.93 | 5.62 | 5.14 | 3.95 |
| Control$^B$ | 6.91 | 5.07 | 4.09 | 2.92 |
| 6$^B$ | 7.08 | 5.59 | 4.76 | 3.43 |
| 7$^B$ | 6.81 | 5.37 | 4.71 | 3.37 |
| 8$^B$ | 6.87 | 5.54 | 4.85 | 3.67 |
| 9 | 6.90 | 5.48 | 4.74 | 3.88 |
| 10 | 6.97 | 5.32 | 4.47 | 3.61 |
| 11 | 6.83 | 5.22 | 4.81 | 3.66 |
| 12 | 6.89 | 5.47 | 4.80 | 3.91 |

| | Mean Log₁₀ Count Reduction from Pre Scrub 1 | | | |
| --- | --- | --- | --- | --- |
| Example | Post Scrub 1 | Post Scrub 2 | Post Scrub 4 | Overall |
| Control$^A$ | 1.57 | 2.27 | 3.33 | 2.39 |
| 6$^A$ | 1.36 | 2.04 | 3.27 | 2.22 |
| 7$^A$ | 1.34 | 1.89 | 3.27 | 2.17 |
| 8$^A$ | 1.31 | 1.79 | 2.98 | 2.03 |
| Control$^B$ | 1.84 | 2.82 | 3.99 | 2.88 |
| 6$^B$ | 1.49 | 2.32 | 3.65 | 2.49 |
| 7$^B$ | 1.44 | 2.10 | 3.44 | 2.33 |
| 8$^B$ | 1.33 | 2.02 | 3.20 | 2.18 |
| 9 | 1.42 | 2.16 | 3.02 | 2.20 |
| 10 | 1.65 | 2.50 | 3.36 | 2.50 |
| 11 | 1.61 | 2.02 | 3.17 | 2.27 |
| 12 | 1.42 | 2.09 | 2.98 | 2.1 |

An objective of this test is to achieve a reduction in microbial counts of at least one log unit (90%) after the first scrub, about two log units (99%) after the second scrub, and about three log units (99.9%) after the fourth scrub. The foregoing results show that the compositions of Examples 6–12 achieved this objective.

Excised Bovine Teat Dip Test

Frozen cow teats from a federally inspected slaughter plant were thawed, trimmed, washed in aqueous Triton X-100 brand of polyethylene glycol p-isooctylphenyl ether (0.25%), rinsed in water, dried with sterile towels, dipped in aqueous alcohol (70%) singed to remove any hair and refrozen for subsequent use. In preparation for use the teats were thawed, dipped in aqueous alcohol (70%) for two minutes and air dried. After being used in the test the teats could be used for a further test on the same day. In preparation for reuse the teats were rinsed in warm water for two minutes, dried with a sterile towel, rinsed with aqueous sodium thiosulfate (0.05%) for one minute, dried again with a sterile towel, rinsed with aqueous lecithin (0.05%) and Tween 80 brand of polysorbate 80 (0.05%) for one minute, dried again with a sterile towel, rinsed in warm water for one minute, dried again with a sterile towel, dipped in aqueous alcohol (70%), and air dried.

One or more of the following microorganisms is found in ninety percent of the cases of bovine mastitis: *Staphylococcus aureus* ATCC 27543, *Streptococcus agalactiae* ATCC 27956, *Streptococcus uberis* ATCC 27958 and *Streptococcus dysgalactiae* ATCC 27957. A pure culture of each of them was grown at 37° C. for 18–24 hours on a brain heart infusion agar slant. Each slant was checked for purity and washed with 2–3 ml. of sterile aqueous proteose-peptone (0.1%). The resulting suspension of microorganism was diluted with the same sterile aqueous proteose-peptone to an optical density of 1.2 at 60 nm and thus a concentration of about $1 \times 10^9$ colony forming units (CFU)/ml. Equal volumes of each of the diluted suspensions were combined and the composite suspension was diluted tenfold with sterile skim milk (10%) and stored at 5° C. so as to contain about $1 \times 10^8$ CFU/ml. of about equal amounts of each of the four microorganisms. The actual concentration was determined by plating in duplicate 1.0 ml. amounts each of $10^5$-fold, $10^6$-fold and $10^7$-fold dilutions of the skim milk composite suspension in sterile aqueous proteose-peptone (0.1%) on soybean-casein digest agar using the pour-plate technique, incubating the plates for 48-72 hours at 37° C., counting the number of CFU on each plate, and calculating the concentration from the results.

Each prepared teat was dipped in the skim milk composite suspension to a depth of 15 mm. Teats serving as untreated controls were allowed to drain for 15 minutes, then sampled. Teats to be treated were allowed to drain for 5 minutes, then dipped in the test composition to a depth of 30 mm., allowed to drain for 10 minutes, and sampled.

Each treated or untreated teat was rinsed with 5 ml. of a quenching solution consisting of Tamol-N Micro brand of condensed naphthalenesulfonic acid sodium salt anionic dispersant (1.0%) in a aqueous sodium phosphate buffer (0.023M, pH=7.2). A 1.0 ml. amount each of the rinse solution and five successive tenfold dilutions thereof in sterile aqueous proteose-peptone (0.1%) was plated on soybean-casein digest agar using the pour-plate technique. The plates were incubated for 48-72 hours at 37° C. and counted.

The results, which are expressed below for the compositions of Examples 13-17 as mean $\log_{10}$ counts of colony forming units on each teat and as mean $\log_{10}$ count reductions from untreated controls, show that all five compositions produced significant mean $\log_{10}$ count reductions from untreated controls on the order of 3 (99.9%).

| Example | Mean $\log_{10}$ Count | Mean $\log_{10}$ Count Reduction |
|---|---|---|
| Control | 6.743 | — |
| 13 | 3.785 | 2.958 |
| Control | 6.988 | — |
| 14 | 4.263 | 2.725 |
| 15 | 3.479 | 3.509 |
| 16 | 3.822 | 3.166 |
| Control | 6.527 | — |
| 17 | 3.632 | 2.895 |

In Vivo Bovine Teat Dip Test

All four teats of 70 cows were exposed twice daily immediately after milking to approximately $5 \times 10^7$ CFU aliquots of weekly fresh cultures of *Staphylococcus aureus* Neubold 305. Immediately after exposure the right front and left rear teats were dipped in the composition of Example 17. The left front and right rear teats were left undipped. All teats were sampled using aseptic technique at least once weekly and the samples were cultured.

A positive case of infection was established by the following criteria: (1) two consecutive weekly samples showing more than 500 CFU/ml. of the infective organism, (2) a single positive sample from a quarter with clinical mastitis, (3) three consecutive weekly samples showing from 100 to 400 CFU/ml. of the infective organism. The following results show that the composition of Example 17 was significantly (p<0.001) effective against infection in the test. Moreover, the treated teats showed no evidence of irritation.

|  | Untreated Teats | Treated Teats |
|---|---|---|
| Number of Teats | 131 | 128 |
| Number of New Infections in First Week | 0 | 0 |
| Number of New Infections in Second Week | 2 | 1 |
| Number of New Infections in Third Week | 13 | 0 |
| Number of New Infections in Fourth Week | 2 | 1 |
| Total Number of Infections | 17 | 2 |
| Percent Infections | 13% | 1.6% |
| Percent Reduction of Infection | — | 87.7% |

Comparative Biological Properties of the Compositions

Comparative examples A-F described below were tested in the above-described excised porcine skin disk dip test. The results were compared with the results set forth above for the compositions of examples 1-5 and 17 of the invention.

COMPARATIVE EXAMPLE A

| Ingredient | Percent by Weight |
|---|---|
| Octenidine Hydrochloride | 0.200 |
| Purified Water to make | 100.0 |

COMPARATIVE EXAMPLE B

| Ingredient | Percent by Weight |
|---|---|
| Coco-Betaine | 1.80 |
| Purified Water to make | 100.0 |

COMPARATIVE EXAMPLE C

| Ingredient | Percent by Weight |
|---|---|
| Myristamine Oxide | 1.80 |
| Purified Water to make | 100.0 |

COMPARATIVE EXAMPLE D

| Ingredient | Percent by Weight |
|---|---|
| Polyquaternium-10 (UCARE Polymer JR 30 M) | 0.550 |
| Purified Water to make | 100.0 |

COMPARATIVE EXAMPLE E

| Ingredient | Percent by Weight |
|---|---|
| Cocaminopropionic Acid | 1.80 |
| Purified Water to make | 100.0 |

COMPARATIVE EXAMPLE F

| Ingredient | Percent by Weight |
| --- | --- |
| Octenidine Hydrochloride | 0.200 |
| PEG-150 Laurate | 12.0 |
| Isopropyl Alcohol | 3.22 |
| Cocamidopropyl Betaine | 5.00 |
| Laneth-16 | 1.00 |
| Edetate Sodium | 0.500 |
| PEG-150 Distearate | 0.500 |
| PEG-2M | 0.100 |
| Perfume | 0.100 |
| Color | 0.00100 |
| Gluconic Acid to make pH 5.8 | — |
| Purified Water to make | 100.0 |

The composition of comparative example F corresponds to example 2 of above-cited Gorman et al. U.S. Pat. No. 4,420,484 except that the octenidine hydrochloride concentration is 0.200% instead of 2.00% to accord with that of present examples 1-5 and 17 and that the pH had to be adjusted downward with gluconic acid instead of upward with sodium hydroxide due to the lower concentration of octenidine hydrochloride.

Comparative examples A-F showed the following results. The control solution was again 25 mM aqueous potassium dihydrogen phosphate. Ten disks were again used for each of the control solution and the tested examples. Standard errors are shown.

| Comparative Example | Mean $Log_{10}$ Count of Bacteria Recovered/Disk | Mean $Log_{10}$ Count Reduction of Bacteria from Control/Disk |
| --- | --- | --- |
| Control A-E | 5.38 ± 0.10 | 0.00 ± 0.10 |
| A | 3.69 ± 0.25 | 1.69 ± 0.25 |
| B | 4.67 ± 0.12 | 0.71 ± 0.12 |
| C | 5.06 ± 0.09 | 0.32 ± 0.09 |
| D | 4.61 ± 0.08 | 0.77 ± 0.08 |
| E | 5.46 ± 0.07 | −0.08 ± 0.07 |
| Control A, F | 5.41 ± 0.05 | 0.00 ± 0.05 |
| A | 3.57 ± 0.18 | 1.84 ± 0.18 |
| F | 4.82 ± 0.08 | 0.59 ± 0.08 |

Statistical analysis of these results by Duncan's multiple range test ($\alpha=0.0001$) shows that the result for comparative example A is significantly different from the result for comparative examples B-E, that is, the antimicrobial effect of a representative compound of Formula I is significantly greater than that of a representative compound of each of Formulas II-V in this test.

Comparison of these results for control A,F and comparative examples A and F with the results shown above for examples 1-5 and the same control shows that a representative compound of each of Formulas II-V does not significantly diminish the antimicrobial effect of a representative compound of Formula I in this test.

Finally, comparison of the result for example 17 (mean $\log_{10}$ count reduction of 1.34±0.14) of the invention with that of comparative example F (mean $\log_{10}$ count reduction of 0.59±0.08) of the prior art shows that the antimicrobial effect of example 17 is significantly greater than that of comparative example F. We believe that this difference is unexpected and unobvious and is due to the diminution of antimicrobial effect of comparative example F by the surfactant combination thereof, a difficulty and disadvantage that has been overcome by the presently described and claimed invention.

We claim:

1. An antimicrobial surface degerming composition consisting essentially of from about 0.01% to about 10% by weight of a bis[4-(R-amino)-1-pyridinium]alkane salt having the structural formula

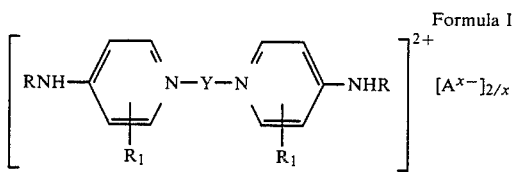

Formula I wherein

Y is alkylene having from 4 to 18 carbon atoms and separating the two 4-(R-amino)-1-pyridinium groups by from 4 to 18 carbon atoms;

R is the same in both occurrences and is alkyl having from 6 to 18 carbon atoms, cycloalkyl having from 5 to 7 carbon atoms, benzyl or phenyl substituted by methylenedioxy or one or two substituents selected from the group consisting of halo, lower-alkyl, lower-alkoxy, nitro, cyano and trifluoromethyl;

$R_1$ is the same in both occurrences and is hydrogen or lower-alkyl;

$A^{x-}$ is a pharmaceutically acceptable anion; and x is the valence of the anion;

(B) from about 0.1% to about 50% by weight of one or more compounds selected from the group consisting of (a) a higher-alkylaminoalkanoic acid having the structural formula

Formula III wherein R is alkyl or alkenyl having from 8 to 18 carbon atoms, R' is hydrogen or $(CH_2)_n$—COOH and n is an integer from 1 to 5 or an alkali metal salt thereof;

(b) a quaternary nitrogen-containing cellulose ether having the structural formula

Formula V wherein $R_{cell}$ is the residue of an anhydroglucose unit ($C_6H_{10}O_5$), x represents the degree of polymerization and is an integer from about 50 to about 20,000 and preferably from about 200 to about 5,000, the R's are the same or different and R has the structural formula

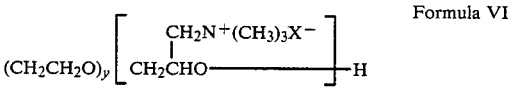

Formula VI wherein y is an integer from 0 to 10, z is an integer from 0 to 3 and $X^-$ is a pharmaceutically acceptable anion; and (C) an aqueous vehicle.

2. The method of degerming a living or nonliving surface which comprises applying to the surface an anti-microbially effective amount of a composition according to claim 1.

3. The method of preventing or treating mastitis in a cow which comprises applying to the teats of the cow after milking a composition according to claim 1.

4. A composition according to claim 1 wherein the bis[4-(R-amino)-1-pyridinium]alkane salt of Formula I is octenidine hydrochloride.

5. A composition according to claim 4 wherein the compound of part B is a compound of Formula III.

6. A composition according to claim 5 wherein the compound of Formula III is Cocaminopropionic Acid.

7. A composition according to claim 4 wherein the compound of part B is a compound of Formula V.

8. A composition according to claim 7 wherein the compound of Formula V is Polyquaternium-10.

9. A composition according to claim 4 wherein the compounds of part B are a compound of Formula III and a compound of Formula V.

10. A composition according to claim 9 wherein the compound of Formula III is Cocaminopropionic Acid and the compound of Formula V is Polyquaternium-10.

11. An antimicrobial bovine teat dip composition consisting essentially of from about 0.1% to about 10% by weight of octenidine hydrochloride, from about 1% to about 20% by weight of Cocaminopropionic Acid, and an aqueous vehicle.

12. The method of preventing or treating mastitis in a cow which comprises dipping the teats of the cow after milking into a composition according to claim 11.

* * * * *